United States Patent
Hanada et al.

(10) Patent No.: US 8,012,415 B2
(45) Date of Patent: Sep. 6, 2011

(54) STERILIZATION METHOD AND PLASMA STERILIZATION APPARATUS

(75) Inventors: Yasushi Hanada, Tomisato (JP); Nobuya Hayashi, Saga (JP)

(73) Assignees: Elk Corporation, Osaka (JP); Saga University, Saga (JP)

( * ) Notice: Subject to any disclaimer, the term of this patent is extended or adjusted under 35 U.S.C. 154(b) by 392 days.

(21) Appl. No.: 12/087,583

(22) PCT Filed: Jan. 11, 2007

(86) PCT No.: PCT/JP2007/050205
§ 371 (c)(1),
(2), (4) Date: Jul. 10, 2008

(87) PCT Pub. No.: WO2007/080907
PCT Pub. Date: Jul. 19, 2007

(65) Prior Publication Data
US 2009/0053101 A1    Feb. 26, 2009

(30) Foreign Application Priority Data
Jan. 11, 2006    (JP) ................. 2006-004166

(51) Int. Cl.
*A61L 2/20*    (2006.01)
*A61L 2/00*    (2006.01)
*A61L 2/18*    (2006.01)
*A61L 9/00*    (2006.01)
*B01J 7/00*    (2006.01)

(52) U.S. Cl. .............. 422/33; 422/28; 422/29; 422/292; 422/306

(58) Field of Classification Search .................... 422/28, 422/29, 33
See application file for complete search history.

(56) References Cited

U.S. PATENT DOCUMENTS
2008/0233002 A1 * 9/2008 Mizuno et al. ............... 422/22

FOREIGN PATENT DOCUMENTS
| | | |
|---|---|---|
| JP | B2-2774193 | 7/1998 |
| JP | A-2000-308675 | 11/2000 |
| JP | A-2004-267524 | 9/2004 |
| JP | A-2005-192574 | 7/2005 |
| JP | A-2006-020950 | 1/2006 |
| WO | WO 92/04057 | 3/1992 |
| WO | WO 2005/094907 A1 | 10/2005 |

* cited by examiner

*Primary Examiner* — Sean E Conley
*Assistant Examiner* — Regina Yoo
(74) *Attorney, Agent, or Firm* — Oliff & Berridge, PLC

(57) ABSTRACT

An object to be sterilized is disposed inside a vacuum chamber, and the inside of the vacuum chamber is evacuated. When the pressure inside the vacuum chamber reaches 3 Pa, a cutoff valve disposed between the vacuum chamber and the vacuum pump is closed. High-frequency power is supplied to an electrode. Oxygen gas is introduced into the vacuum chamber for 0.1 sec. Thereafter, the pressure is held constant for 3 sec. Until the pressure inside the vacuum chamber reaches 10 kPa, introduction of oxygen gas into the vacuum chamber is repeated. When the pressure reaches 10 kPa, the cutoff valve is opened to evacuate the inside of the vacuum chamber and the supply of the high-frequency power is stopped. Introducing the oxygen gas and determining pressure inside the vacuum chamber is repeated, and after 90 min, the pressure inside the vacuum chamber is returned to atmospheric pressure.

3 Claims, 7 Drawing Sheets

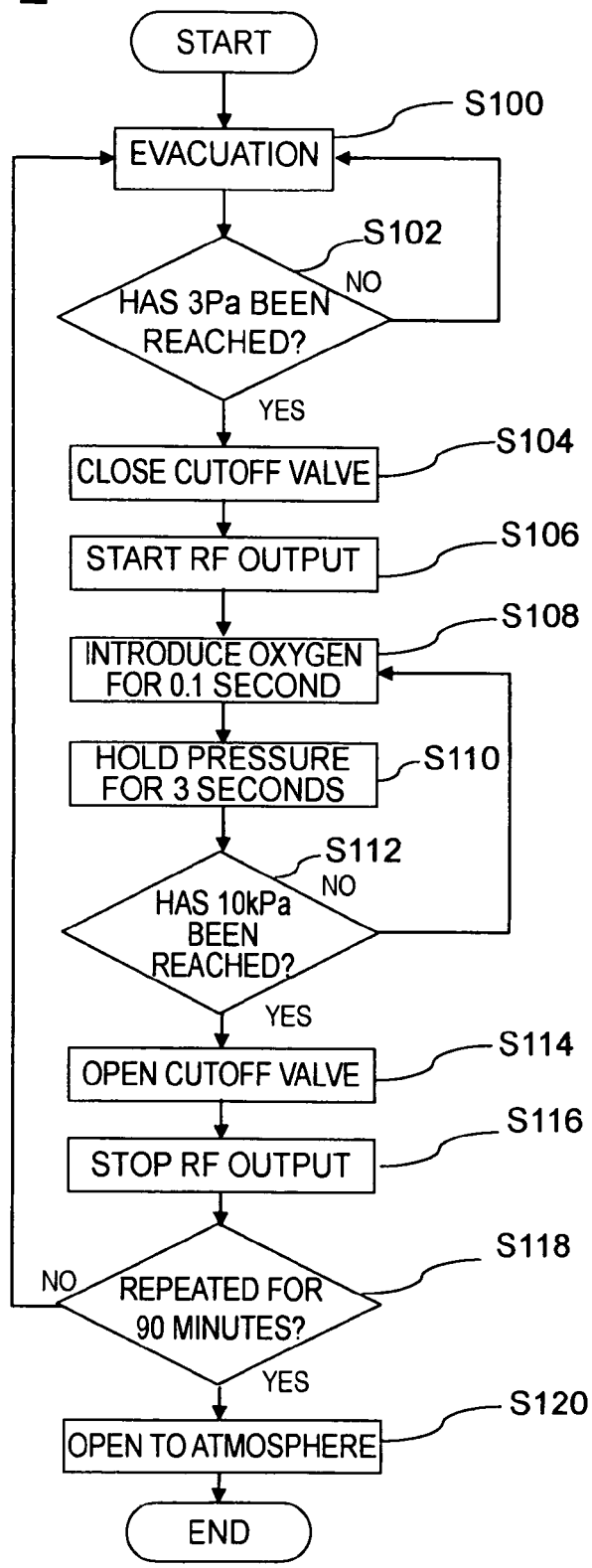
F I G. 2

F I G . 3
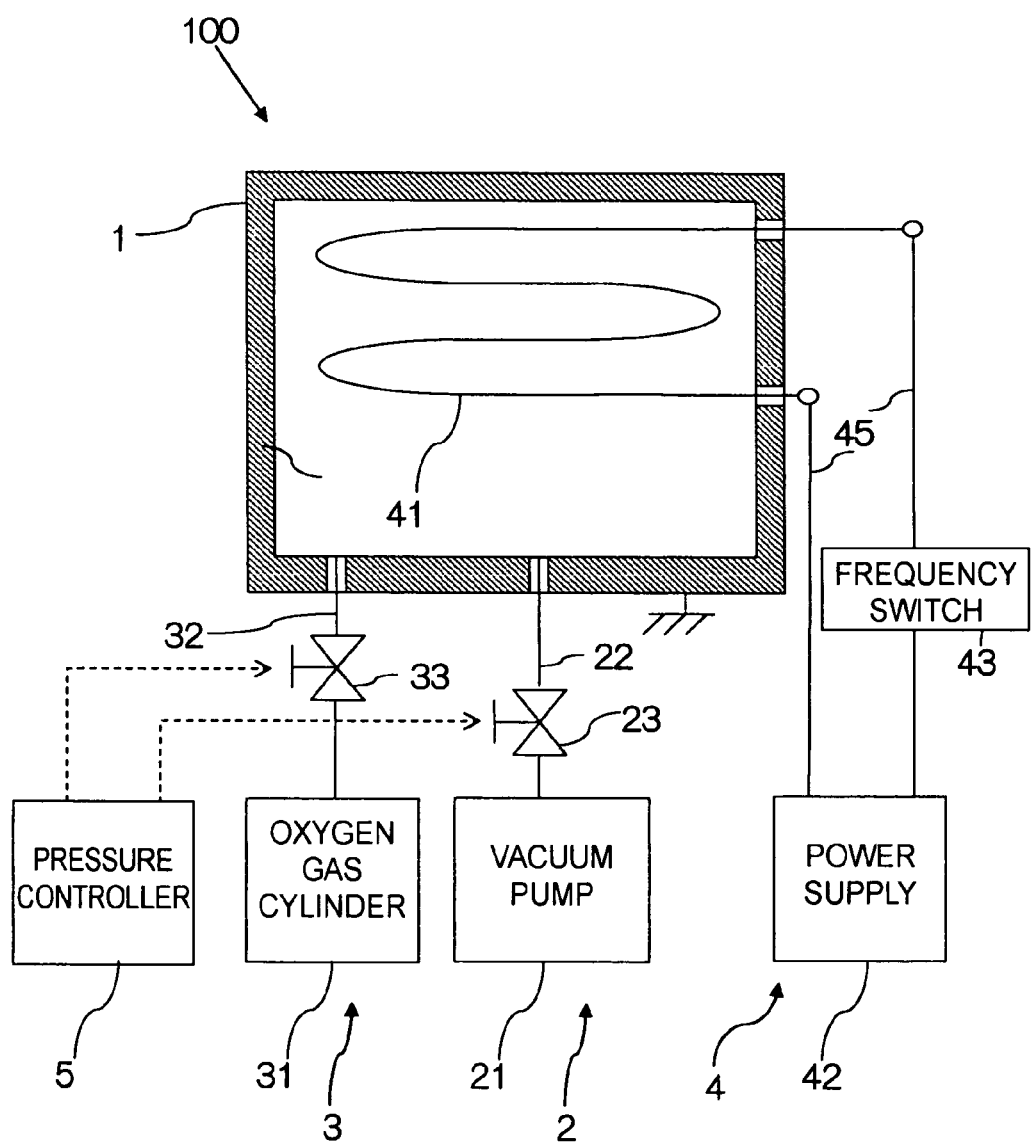

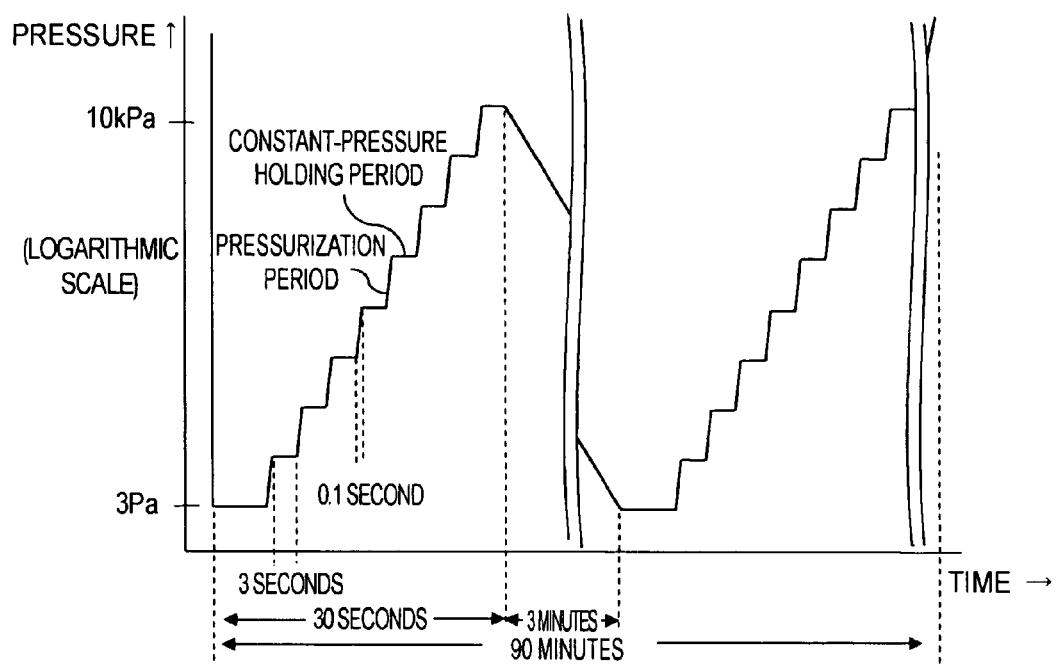
F I G . 4

F I G . 5
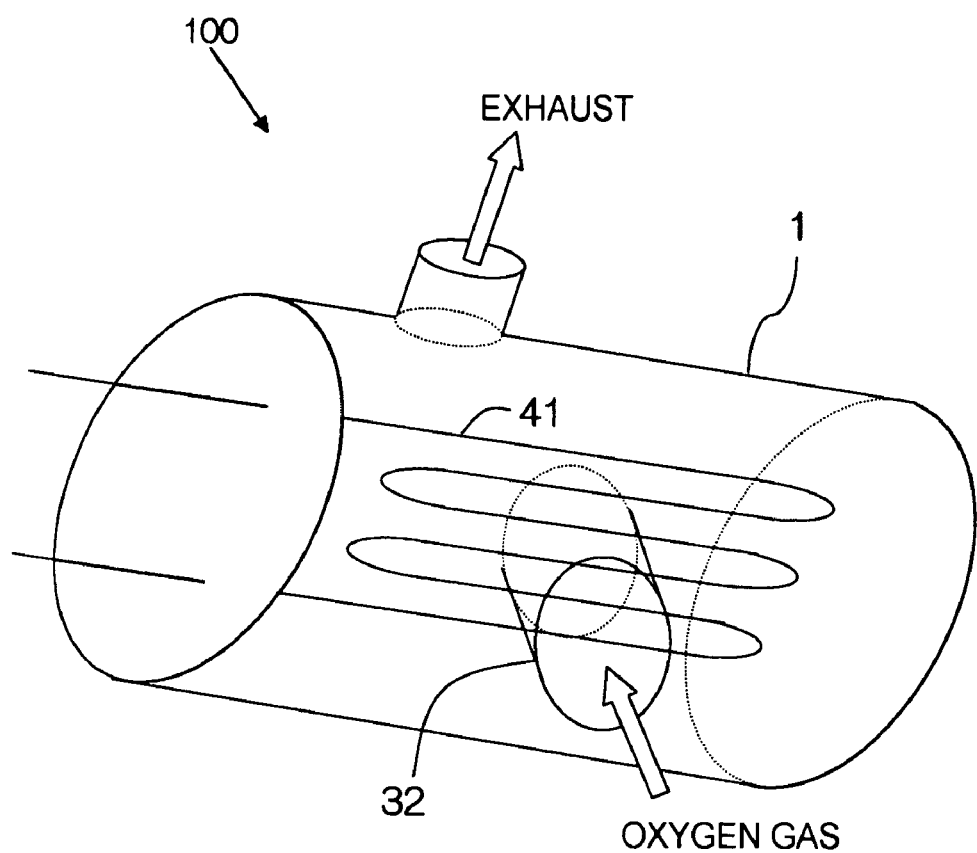

F I G. 6
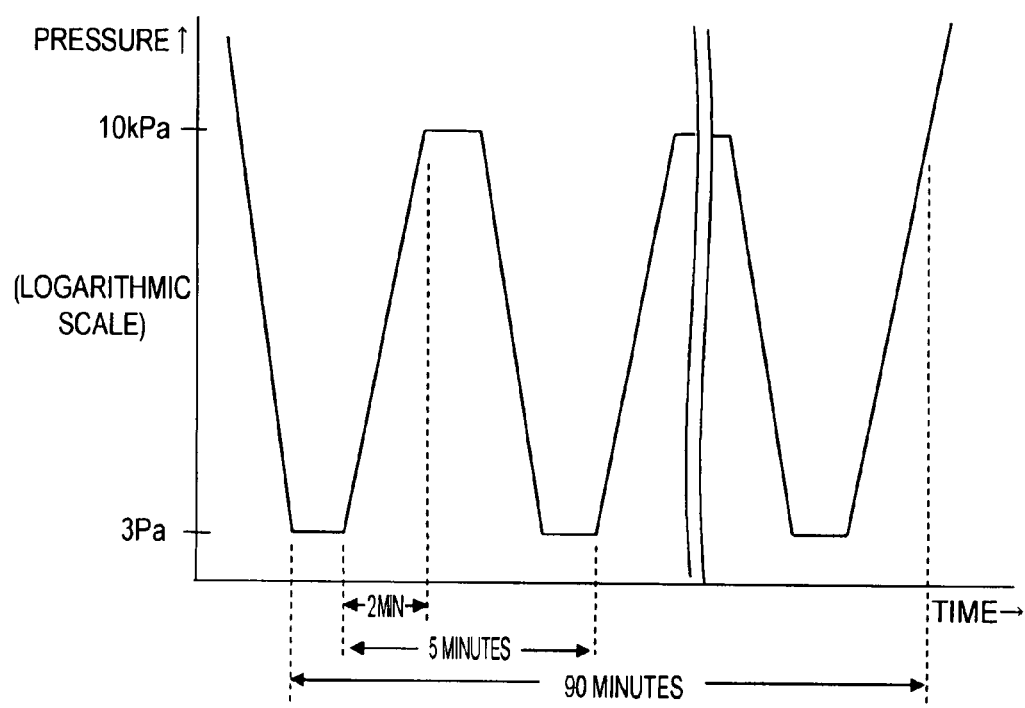

Chemical Indicator Strip

Chemical Indicator Strip

Chemical Indicator Strip

Chemical Indicator Strip

STERILIZATION METHOD AND PLASMA STERILIZATION APPARATUS

TECHNICAL FIELD

The present invention relates to a sterilization method which uses a plasma and to a plasma sterilization apparatus, and more particularly to a method and apparatus which can be used for sterilizing medical devices and the like.

BACKGROUND ART

Sterilization methods which use plasma are effective for sterilizing medical devices and the like.

Known plasma sterilization methods include sterilization treatment that involves using hydrogen peroxide and converting it to a plasma. However, hydrogen peroxide is a liquid at room temperature, and the introduction of a liquid into a low-pressure plasma chamber complicates both the structure of the apparatus and pressure regulation. Moreover, hydrogen peroxide is expensive, and so the high costs incurred by its use pose an additional challenge. Also, because hydrogen peroxide is an irritant, accidents (burns) due to the leakage or scattering of liquid are a constant concern.

Hence, the use of an oxygen-containing gas mixture has been disclosed in Patent Document 1 below as a substitute for hydrogen peroxide. However, reliably sterilizing an object with a gas mixture that has been converted to plasma is difficult, and it has not been possible to achieve adequate sterilization effects in this way. Also, increasing the number of gases used has made the construction of the apparatus more complex. Patent Document 2 below, which was disclosed in light of such circumstances, relates to the use of an oxygen-based gas alone rather than a gas mixture.

Patent Document 1: Japanese Patent Publication No. 2774193

Patent Document 2: Japanese Unexamined Patent Publication No. 2004-267524

DISCLOSURE OF THE INVENTION

Problems to be Solved by the Invention

However, in the invention described in above Patent Document 2, in the course of feeding $O_2$ gas to a vacuum chamber, the $O_2$ gas is passed through an ozone generator where ozone is introduced into the $O_2$ gas. As a result, the apparatus has a more complicated construction than one in which a simple, unmixed gas is fed by itself. Because the particles (e.g., radicals) in the plasma which have a sterilizing ability have short life time, lasting perhaps 0.1 second, they have not hitherto had a thoroughly sterilizing effect. Sterilization in this way has thus been very inadequate, particularly in the case of objects with a tubular or other shape having a lumen.

Accordingly, it is an object of the present invention to provide a sterilization method and a plasma sterilization apparatus which, although simply configured, are capable of thoroughly sterilizing in particular objects having a lumen.

Means for Solving the Problems

To achieve the foregoing objects, the sterilization method and plasma sterilization apparatus of the invention are configured in such a way that, when the interior of a vacuum chamber where a plasma is to be generated is pressurized by the introduction of a specific gas, the pressure is increased in a stepwise manner by providing pressurization periods and constant-pressure holding periods.

Accordingly, the sterilization method of the present invention includes: placing a specific object to be sterilized inside a vacuum chamber; evacuating the vacuum chamber to a specific pressure; causing a specific gas to flow into the vacuum chamber; generating a plasma having a sterilizing ability inside the vacuum chamber; and using the generated plasma and sterilizing the object to be sterilized while the pressure inside the vacuum chamber is regulated. The pressure inside the vacuum chamber is regulated in such a way that pressurization is carried out, with a pressurization period and a constant-pressure holding period being provided at a specified pressure interval. Periods in which the pressure decreases may be included as part of the pressure changes inside the vacuum chamber. As used herein, "constant-pressure holding period" is not limited to periods in which the pressure is fixed throughout the period, and encompasses also periods in which the degree of pressure change is much smaller than in the pressurization period.

It is desirable for the specified pressure interval to be a value in a range of from 10 Pa to 1 kPa.

The constant-pressure holding period is preferably from 0.3 to 10 seconds, and more preferably from 0.5 to 3 seconds.

It is desirable for the specific gas to be composed of oxygen, and for each pressurization period to be set to a length of from 0.01 to 1.5 seconds.

The plasma sterilization apparatus of the invention includes: a vacuum chamber; pressure regulating means for regulating pressure inside the vacuum chamber; gas supply means for causing a specific gas to flow into the vacuum chamber; and plasma generating means for generating plasma having a sterilizing ability inside the vacuum chamber. The pressure regulating means has a pressure controller which, during plasma generation, increases the pressure inside the vacuum chamber, with a pressurization period and a constant-pressure holding period being provided at a specified pressure interval.

It is desirable for the specified pressure interval to be a value in a range of from 10 Pa to 1 kPa.

The pressure regulating means preferably has a vacuum pump and, a passage opening and closing member, disposed on an exhaust passage between the vacuum chamber and the vacuum pump, for opening and closing the exhaust passage.

It is desirable for the passage opening and closing member to be a cutoff valve.

The specific gas is preferably composed of oxygen gas.

Effects of the Invention

In the sterilization method and plasma sterilization apparatus of the present invention, the pressure inside the vacuum chamber is regulated in such a way that pressurization is carried out while providing, at a specified pressure interval, a pressurization period and a constant-pressure holding period. This enables particles having a sterilizing ability to be sufficiently generated in the constant-pressure holding period. In the pressurization period, a pressure difference can be generated, thereby making it possible to generate rapid flow within the plasma. It is thus possible to both efficiently generate a plasma having a sterilizing effect and also, even when the object to be sterilized has a lumen, to cause the plasma having a sterilizing ability to reach deep into the lumen, enabling effective sterilization to be carried out.

BRIEF DESCRIPTION OF THE DRAWINGS

FIG. 2 is a flow chart explaining the sterilization method used in the examples.

FIG. 3 is schematic view of the plasma sterilization apparatus in Example 1.

FIG. 4 is a timing chart showing the relationship between stepwise pressure changes and time in Example 1.

FIG. 5 is a schematic view of the plasma sterilization apparatus in Example 2.

FIG. 6 is a conceptual diagram showing the relationship between pressure changes and time described in an earlier patent application.

EXPLANATIONS OF LETTERS AND NUMERALS

1 VACUUM CHAMBER
2 PRESSURE REDUCING MEANS
3 OXYGEN GAS FEEDING MEANS
4 DISCHARGE PLASMA GENERATING MEANS
5 PRESSURE CONTROLLER
21 VACUUM PUMP
22 EXHAUST PASSAGE
23 REGULATING VALVE
31 OXYGEN GAS CYLINDER
32 FEED LINE
33 REGULATING VALVE
41 ELECTRODE
42 POWER SUPPLY
43 FREQUENCY SWITCH
45 COAXIAL CABLE
100 PLASMA STERILIZATION APPARATUS

BEST MODE FOR CARRYING OUT THE INVENTION

Figure 1:
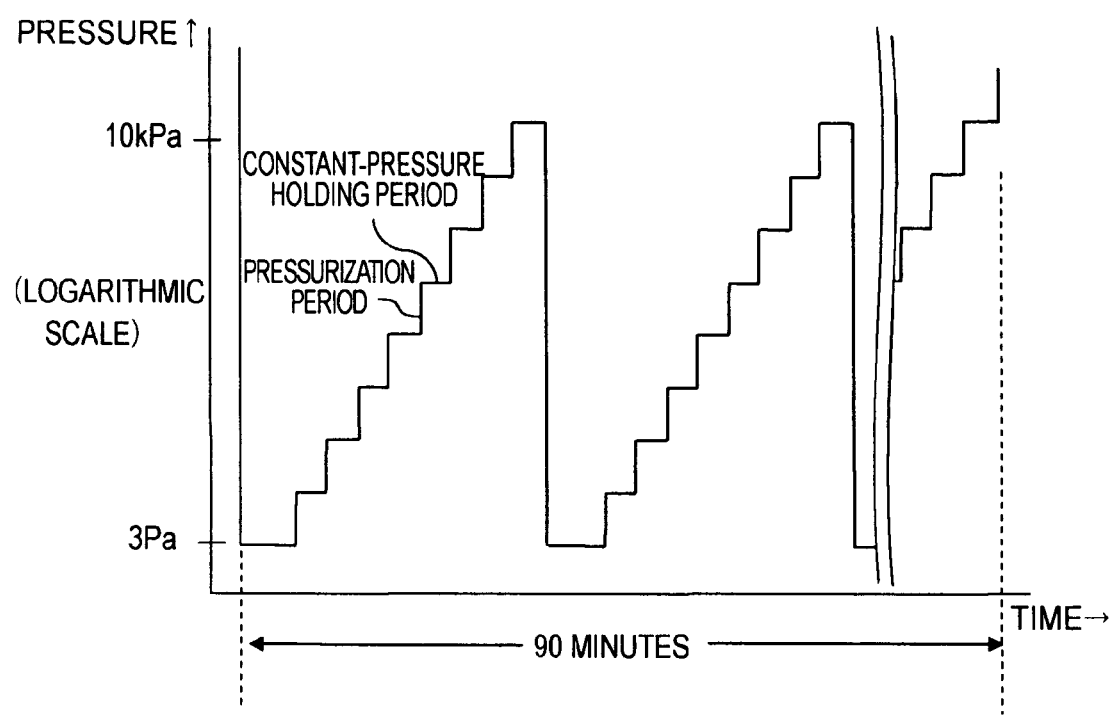
FIG. 1 is a conceptual diagram showing the relationship between stepwise pressure changes and time in an embodiment of the invention.

Specific embodiments of the invention are described below, starting with the sterilization method and followed by the plasma sterilization apparatus.
<Sterilization Method>
The sterilization method of the present embodiment entails carrying out sterilization by reducing the pressure inside a vacuum chamber in which a specific object to be sterilized (e.g., a medical device) has been placed to a specific pressure, then causing a specific gas to flow into the vacuum chamber and generating a plasma having a sterilizing ability. In this process, the pressure inside the vacuum chamber after the plasma has been generated is regulated so as to rise in a stepwise fashion by providing, at a specified pressure interval, a pressurization period and a constant-pressure holding period. The sterilization effects can thereby be increased. FIG. 1 is a conceptual diagram showing the relationship between the above-described stepwise pressure changes and time. Referring to FIG. 1, the interior of the vacuum chamber is first evacuated to, for example, 3 Pa, following which stepwise pressurization is carried out up to, for example, 10 kPa, after which the pressure is again reduced to 3 Pa. This cycle is repeated over a period of 90 minutes. Particles which exhibit a sterilizing ability (generally thought to be radicals, and thus also referred to below as "radicals"; however, such "particles" are not limited to radicals and also encompass herein active species and all other particles which are generated in connection with a plasma and exhibit a sterilizing ability) are generated in this way during the constant-pressure holding period, in addition to which rapid flow due to the pressure change in the pressurization period is generated within the plasma, thereby efficiently generating a plasma having a sterilizing ability and also enabling such particles to flow deep into the object to be sterilized. As a result, it is possible to carry out thorough sterilization, and in particular the reliable sterilization even of wall areas at the tip of a lumen (e.g., in a tubular object which is closed at one end).

By setting the specified pressure interval to a value within a range of from 10 Pa to 1 kPa, it is possible to improve the flow of particles deep into the object to be sterilized.

Here, with regard to the relationship between pressure and time in the pressurization period, letting the change in pressure during this pressurization period be $\Delta p$ (Pa) and the change in time be $\Delta t$ (seconds), the slope $\Delta p/\Delta t$ is preferably set in a range of from 10 Pa/s to 10 kPa/s. This slope may be set to the same value for all pressurization periods, or may be individually set as appropriate for each pressurization period.

By setting the constant-pressure holding period to from 0.3 to 10 seconds, particles can be effectively generated. The lower limit has been set to 0.3 second after taking into account the response rate of the valve or the like used in vacuum chambers today. The upper limit has been set to 10 seconds so as to ensure that, during the pressurization periods, the plasma is made to flow a sufficient number of times into the object to be sterilized. It is more preferable to set the constant-pressure holding period to from 0.5 to 3 seconds. When the response rate of valves or the like used in vacuum chambers today is taken into account, the constant-pressure holding period must be set to at least 0.3 second. However, the lower limit in the constant-pressure holding period is not, of course, limited to this value; with improvements in the response rate of valves or the like, the constant-pressure holding period may be set to less than 0.3 second (provided the resulting period allows sufficient particles exhibiting a sterilizing ability to be generated).

Next, mathematical formulas are used to explain the advantages of the present embodiment in cases where sterilization is carried out by introducing, into a luminal tube as the body to be sterilized, a plasma (radicals) having a sterilizing ability within the above-described specific gas.

First, there is furnished a body to be sterilized which is composed of a luminal tube of radius r and length L to one end of which is connected a closed cylindrical tube of radius 4r and length L/5. Here, r and L are respectively set to, for example, 2 mm and 50 mm. The body to be sterilized is arranged in a specific place inside the sterilizer chamber, the pressure is reduced to a specific pressure of, for example, 3 Pa, and a specific gas is introduced in this state until a pressure of, for example, 10 kPa is reached.

In the course of introducing the specific gas, as the pressure rises inside the luminal tube of the body to be sterilized, gas continuously flows into the luminal tube. Here, letting the change in pressure per unit time be $\Delta P1$ ($P1 \Rightarrow P2$), if the distance that the gas moves in response to $\Delta P1$ is $\Delta N1$ ($N1 \Rightarrow N2$), for example, 10 mm, the volume of gas that flows in per unit time is expressed by the formula (1) below.

Formula (1)

$$\int_{w1}^{w2} \int_{-r}^{+r} \sqrt{(r^2 - X^2)} \, dr \, dX \tag{1}$$

Here, letting the unit time for gas inflow be 1 second and letting the gas be $O_2$, because the life of oxygen radicals is about 0.1 second, even when there has been a continuous inflow of oxygen radicals in response to a continuous change in pressure, the distance of inflow by the oxygen radicals from the mouth of the luminal tube in the body to be sterilized is at most only (N1→N2)/10. The volume of inflow by oxygen radicals is thus expressed by formula (2) below, and becomes constant regardless of the length of time that elapses.

Formula (2)

$$\int_{w1/10}^{w2/10} \int_{-r}^{+r} \sqrt{(r^2-X^2)}\, dr\, dX \quad (2)$$

Here, when there is a desire to have the oxygen radicals reach deep into the luminal tube of the body to be sterilized, the pressure change per unit time ΔP1 must be set so as to be even faster.

That is, if the pressure change per unit time ΔP1 is made ten times faster, for example, this will be accompanied by a ten-fold increase in the distance ΔN1 that the gas moves. As a result, in keeping with formula (3) below, the volume of gas that moves per unit time also becomes ten-fold.

Formula (3)

$$10\int_{w1/10}^{w2/10} \int_{-r}^{+r} \sqrt{(r^2-X^2)}\, dr\, dX \quad (3)$$

In addition, as indicated by formula (4) below, proportional with this, the volume of oxygen radicals that moves also increases ten-fold.

Formula (4)

$$\int_{w1}^{w2} \int_{-r}^{+r} \sqrt{(r^2-X^2)}\, dr\, dX \quad (4)$$

However, because oxygen radicals are generated by the collision of ionized electrons with oxygen molecules, it is essential that the oxygen molecules remain in this environment until such time as they collide with electrons and turn into radicals. If this period is too short, sufficient radicals will not be obtained even within a plasma environment, and the gas that flows into the luminal tube of the body to be sterilized will be composed of ordinary oxygen molecules rather than oxygen radicals. That is, increasing the pressure change rate ten-fold leads to the inflow of gas in a state where oxygen radicals are not sufficiently generated. In short, when a pressure change rate is selected that allows for the sufficient generation of oxygen radicals, the distance reached by the oxygen radicals shortens; conversely, when the pressure change rate is raised so as to increase the distance reached by the oxygen radicals, sufficient oxygen radicals are not generated.

In the sterilization method of the present embodiment, constant-pressure holding periods in which the pressure is not changed and pressurization periods in which the pressure is rapidly changed are alternately provided in the course of pressure change, thus adroitly solving the above problems by generating a sufficient amount of radicals in the constant-pressure holding period and enabling the radicals to flow deep into the luminal tube of the body to be sterilized in the pressurization period in which the pressure is rapidly changed. In this way, even when the inflow volume of the above-described radicals expressed by formula (2) is increased ten-fold, as indicated in formula (4), the radicals can be introduced deep into the luminal tube of the body to be sterilized, enabling sterilization of the body to be reliably carried out.

<Plasma Sterilization Apparatus>

The plasma sterilization apparatus of the present embodiment has a vacuum chamber, means for regulating pressure inside the vacuum chamber by adjusting the gas flow rate and/or the vacuum pump discharge rate, means for causing a specific gas to flow into the vacuum chamber, and means for generating plasma having a sterilizing ability inside the vacuum chamber. Here, the pressure regulating means regulates the pressure inside the vacuum chamber following plasma generation by providing, at a specified pressure interval, a pressurization period and a constant-pressure holding period so as to effect stepwise pressurization, in this way increasing the sterilization effects. The pressure regulating means has a CPU and a memory for storing a specific pressure regulating program.

Setting the specified pressure interval to a value in a range of from 10 Pa to 1 kPa enables the flow of particles deep into the body to be sterilized to be enhanced.

Letting the change in pressure during this pressurization period be Δp (Pa) and the change in time be Δt (seconds), the slope Δp/Δt is preferably set in a range of from 10 Pa/s to 10 kPa/s. This slope may be set to the same value in all pressurization periods, or may be individually set as appropriate for each pressurization period.

Pressure regulation inside the vacuum chamber can be more easily carried out by providing, on an exhaust passage between the vacuum chamber and the vacuum pump, a cutoff valve which opens and closes the exhaust passage.

The term "sterilization" used in the specification refers to treatment which reduces the total bacterial cell count following sterilization treatment to $10^{-6}$ times or less of the total bacterial cell count before sterilization treatment. Such a definition for "sterilization" agrees with that given in *Guidelines for Sterility Assurance* (published by Japanese Society of Medical Instrumentation in September 2005).

The present inventor earlier disclosed, in Japanese Patent Application No. 2004-203419 (filed on Jul. 9, 2004), a plasma sterilization apparatus. Oxygen gas inside a vacuum apparatus is converted to a plasma, after which a plurality of pressurization-evacuation cycles in which the pressure of the oxygen gas is first raised from 3 Pa to 10 kPa then lowered to 3 Pa are repeated. In this respect, the earlier patent application shares common features with the present embodiment. FIG. 6 shows a conceptual diagram of the pressurization-evacuation cycle in the earlier application, which was conceived in order to increase the efficiency of sterilization relative to the art at the time.

However, the apparatus described in Japanese Patent Application No. 2004-203419 and the apparatus of the present embodiment differ definitively with regard to whether or not a constant-pressure holding period is provided at the time of pressurization from 3 Pa to 10 kPa. When a constant-pressure holding period is not provided, as in the disclosure of Japanese Patent Application No. 2004-203419, particles (radicals) which exhibit a sterilizing ability cannot be sufficiently generated by causing flow to occur continuously within plasma. On the other hand, in the apparatus of the present embodiment, by providing a plurality of constant-pressure holding periods and intermittently creating small flow states, particles (radicals) which exhibit a sterilizing ability can be generated both in a larger number and continuously. By also providing, between one constant-pressure holding period and another constant-pressure holding period, a pressurization period in which the pressure is rapidly raised, rapid flow is generated within the plasma, making it possible to cause particles (radicals) which exhibit a sterilizing ability to rapidly flow through the body to be sterilized, thus greatly enhancing the sterilization effect.

The reason is presumably that, although particles (radicals) which exhibit a sterilizing ability are constantly being generated, because they have short life time, most of the particles have difficulty reaching deep into the body to be sterilized. It is thus important, as in the present embodiment, to generate a larger number of particles by providing constant-pressure holding periods, and to generate rapid flow within the plasma by providing pressurization periods which carry out rapid pressurization.

The apparatus disclosed in Japanese Patent Application No. 2004-203419 carries out sterilization with an electrical discharge plasma. In the present embodiment as well, it is preferable to generate the plasma by means of electrical discharge.

Moreover, although art which entails the generation of pressure changes in a plasma sterilization apparatus so as to give rise to alternating, cyclic low-pressure periods and high-pressure periods is already known, the pressure changes in such a case differ both in their aim and constitution from the present embodiment in which efficient sterilization treatment is carried out by providing alternating pressurization periods and constant-pressure holding periods.

EXAMPLES

Examples are given below to more fully illustrate the sterilization method and the plasma sterilization apparatus of the present invention. The above-indicated definition of "sterilization" is satisfied in all the examples.

Example of Sterilization Method

The sterilization method used in the example is described in conjunction with the flow chart shown in FIG. 2.

First, the object to be sterilized is placed in a vacuum chamber and the pressure inside the chamber is reduced (S100). The program then determines whether the pressure in the vacuum chamber has reached 3 Pa (S102). If it is determined that this pressure has been reached, the cutoff valve situated between the vacuum chamber and the vacuum pump is closed (S104). Next, RF power is fed (S106) to an electrode, oxygen gas is introduced into the vacuum chamber for a period of 0.1 second (S108), then the pressure is held constant for 3 seconds (S110). The program then determines whether the pressure in the vacuum chamber has reached 10 kPa (S112), and steps S108 to S112 are each repeated until a pressure of 10 kPa is reached. Once the interior of the vacuum chamber has reached a pressure of 10 kPa, the cutoff valve is opened so as to evacuate the vacuum chamber (S114), and the supply of RF power is stopped (S116). The respective steps S100 to S118 are repeated from the moment that it is initially determined in step S102 that a pressure of 3 Pa has been reached until 90 minutes have elapsed. Once 90 minutes have elapsed, the interior of the vacuum chamber is returned to atmospheric pressure and the body to be sterilized is removed (S120). By passing through this process, thorough sterilization, and, in particular, reliable sterilization of a lumen, can be carried out.

The present invention is not limited to the above-mentioned values, i.e., an oxygen introducing time of 0.1 second, a sterilization time of 90 minutes and a pressure inside the vacuum chamber of from 3 Pa to 10 kPa. Optimal values may be suitably selected for each.

For example, the above oxygen introducing time may be set to any value within a range of from 0.01 to 1.5 seconds.

Example 1 of Plasma Sterilization Apparatus

FIG. 3 shows a schematic diagram of a plasma sterilization apparatus according to Example 1. This plasma sterilization apparatus 100 has a vacuum chamber 1 in which a medical device or the like (not shown) to serve as the object of sterilization is placed, pressure reducing means 2 for reducing the pressure in the vacuum chamber 1, oxygen gas feeding means 3 for feeding oxygen gas into the vacuum chamber 1, discharge plasma generating means 4 for generating a plasma inside the vacuum chamber 1, and a pressure controller 5 for controlling the oxygen gas feeding means 3 and the discharge plasma generating means 4. The pressure-reducing means 2 is composed of a vacuum pump (rotary pump) 21 which discharges gases from the vacuum chamber 1, an exhaust passage 22 which communicates between the vacuum chamber 1 and the vacuum pump 21, and a regulating valve (e.g., a cutoff valve) 23 which is situated on the exhaust passage for regulating the amount of gases discharged. The oxygen gas feeding means 3 is composed of an oxygen gas cylinder 31, a feed line 32 which communicates between the vacuum chamber 1 and the oxygen gas cylinder 31, and a regulating valve (e.g., a mass flow controller) 33 which is located on the feed line 32 and regulates the flow rate of oxygen gas. The discharge plasma generating means 4 is composed of an electrode 41, a power supply 42 which feeds RF power to the electrode 41, a coaxial cable 45 which transmits power from the power supply 42 to the electrode 41, and a frequency switch 43 which selectively switches the frequency of RF power output from the power supply 42 between 10 kHz and 13.56 MHz.

The frequency switch 43 is adapted for switching the frequency to 10 kHz when plasma is initially generated during the supply of RF power to the electrode 41 and, after 1 to 2 minutes have elapsed thereafter, for switching the frequency to 13.56 MHz.

The pressure controller 5 controls the regulating valve (e.g., cutoff valve) 23 so as to enable regulation of the discharge rate of gases inside the vacuum chamber 1, and also controls the regulating valve (e.g., mass flow controller) 33 so as to enable regulation of the gas flow rate. The gas flow rate is set to a value of from 10 to 500 sccm.

FIG. 4 is a timing chart showing the relationship between the stepwise pressure changes and time in Example 1 (the same applies to Example 2 as well). That is, inside the vacuum chamber 1 of the plasma sterilization apparatus 100 configured as described above, as shown in FIG. 4, the operations of, first, introducing oxygen gas for 0.1 second, then holding the pressure constant for 3 seconds are repeated for 30 seconds, thereby raising the pressure inside the vacuum chamber 1 to 10 kPa, after which the pressure is reduced once again to 3 Pa over a period of 3 minutes. By repeating this sequence of operations, which constitutes one cycle, for a period of 90 minutes, sufficient sterilization, particularly the sterilization of lumens, can be carried out.

The oxygen introducing time of 0.1 second, the 10 kPa to 3 Pa pressure-reducing time of 3 minutes, the sterilization time of 90 minutes, and the pressure range of 3 Pa to 10 kPa inside the vacuum chamber 1 are not limitative values. Optimal values may be suitably selected for each.

Example 2 of Plasma Sterilization Apparatus

FIG. 5 shows a schematic diagram of a plasma sterilization apparatus according to Example 2. Elements in the apparatus of Example 2 having the same function as elements in Example 1 are denoted by like reference numbers, and detailed descriptions of those elements are omitted below.

In the plasma sterilization apparatus 100 of Example 2, the electrode 41 is disposed at a different position than in the plasma sterilization apparatus of Example 1. This electrode 41 is disposed in such a way that oxygen gas fed from the feed line 32 passes through the vicinity of the electrode 41. As a result, plasma generation can be better promoted.

In this example as well, by changing the pressure in a stepwise manner as shown in FIG. 4, thorough sterilization, particularly the sterilization of lumens, can be carried out.

In the above examples, only plasma generating means based on electrical discharge are mentioned. However, the plasma generating means is not limited to electrical discharge (e.g., CCP (Capacitively Coupled Plasma), microwave plasma). Various other types of plasma generating means may also be suitably used. For example, the plasma may be generated by ultraviolet light, ionizing radiation, shock waves, or thermal contact.

The gas employed is not limited to oxygen. Any active gas having an oxidizing ability may be used. For example, use may be made of ozone, carbon dioxide, water or alcohol.

The object to be sterilized is not limited to an inert object such as a medical device, and may also be an organic object such as living tissue.

By covering the object to be sterilized with a sheet (e.g., a micromesh sheet) that is permeable to the particles (radicals) which exhibit a sterilizing ability but impermeable to bacteria and carrying out sterilization, external bacteria can be prevented from re-depositing on the object when it is removed from the vacuum chamber 1 following treatment.

In addition, the shape of the electrode 41 is not limited to the shape in the above-described examples. Use can also be made of electrodes having other shapes, such as solenoids.

EXPERIMENTAL EXAMPLES

A syringe with a chemical indicator (CI) strip inserted therein was set inside a sterilization vacuum chamber having a capacity of 40 L (liter), and sterilization gas (radicals) was introduced in a variety of pattern into the vacuum chamber, following which the change in the CI strip due to the influence of the sterilization gas was measured in each case. Ordinarily, the greater the influence by the sterilization gas, the larger the degree of color change (e.g., change from orange to yellow) by the reagent-coated portion of the CI strip. However, in the CI strips shown in FIGS. 7 to 10, for the sake of convenience, the color changes have been converted to intensity changes and shown schematically (with slight modifications for greater visibility). That is, a lower CI intensity indicates a larger influence by the sterilization gas.

Experimental Example 1 (Comparative Example)

Figure 7:
FIG. 7 is a diagram which schematically shows the chemical indicator CI change in Experimental Example 1 (comparative example).

The (2-minute) operation of lowering the pressure inside the vacuum chamber to 10 Pa, then introducing oxygen up to a pressure of 600 Pa and again reducing the pressure to 10 Pa was repeated for 120 minutes without providing constant-pressure holding periods. FIG. 7 shows the CI strip in this case after it changed.

Experimental Example 2 (Example (a))

Figure 8:
FIG. 8 is a diagram which schematically shows the CI change in Experimental Example 2 (Example (a)).

The operation of lowering the pressure inside the vacuum chamber to 10 Pa, then providing alternating 150 msec oxygen introducing periods in which oxygen was introduced to a pressure of 600 Pa and 1500 msec constant-pressure holding periods, and again reducing the pressure to 10 Pa was repeated for 120 minutes. FIG. 8 shows the CI strip in this case after it changed.

Experimental Example 3 (Example (b))

Figure 9:
FIG. 9 is a diagram which schematically shows the CI change in Experimental Example 3 (Example (b)).

The operation of lowering the pressure inside the vacuum chamber to 10 Pa, then providing alternating 100 msec oxygen introducing periods in which oxygen was introduced to a pressure of 600 Pa and 1500 msec constant-pressure holding periods, and again reducing the pressure to 10 Pa was repeated for 120 minutes. FIG. 9 shows the CI strip in this case after it changed.

Experimental Example 4 (Example (c))

Figure 10:
FIG. 10 is a diagram which schematically shows the CI change in Experimental Example 4 (Example (c)).

The operation of lowering the pressure inside the vacuum chamber to 10 Pa, then providing alternating 50 msec oxygen introducing periods in which oxygen was introduced to a pressure of 600 Pa and 1500 msec constant-pressure holding periods, and again reducing the pressure to 10 Pa was repeated for 120 minutes. FIG. 10 shows the CI strip in this case after it changed.

RESULTS

As is apparent from the above experimental examples, larger sterilization gas effects were achieved at the interior of the syringes in the examples of the invention than in the comparative example.

Moreover, on comparing Examples (a), (b) and (c), it can be seen that by shortening each oxygen introducing period and correspondingly increasing the number of oxygen introducing periods in which oxygen is introduced until a pressure of 600 Pa is reached, it was possible to further increase the effects by the sterilizing gas.

The invention claimed is:

1. A sterilization method comprising: placing a specific object to be sterilized inside a vacuum chamber; evacuating the vacuum chamber to a specific pressure; causing a specific gas to flow into the vacuum chamber; generating a plasma having a sterilizing ability inside the vacuum chamber; and using the generated plasma and sterilizing the object to be sterilized while the pressure inside the vacuum chamber is regulated, wherein the pressure inside the vacuum chamber is regulated in such a way that, in the course of pressurization until a specific pressure is reached, pressurization is carried out by stepwise pressurization having a plurality of specified pressure intervals, each pressure interval having a pressurization period and a constant-pressure holding period;

the specific gas comprises oxygen; and each pressurization period is set to a length of from 0.01 to 1.5 seconds.

2. The sterilization method according to claim 1, wherein each specified pressure interval is a value in a range of from 10 Pa to 1 kPa.

3. The sterilization method according to claim 1, wherein the constant-pressure holding period is from 0.3 to 10 seconds.

* * * * *